United States Patent [19]
Garfield et al.

[11] Patent Number: 6,028,106
[45] Date of Patent: Feb. 22, 2000

[54] TREATMENT OF URINARY INCONTINENCE WITH NITRIC OXIDE SYNTHASE SUBSTRATES AND/OR NITRIC OXIDE DONORS ALONE OR IN COMBINATION WITH ESTROGEN OR PROGESTERONE AND/OR OTHER AGENTS

[75] Inventors: Robert E. Garfield, Friendswood, Tex.; Kristof Chwalisz, Berlin, Germany

[73] Assignees: Schering Aktiengesellschaft, Berlin, Germany; Board of Regents, The Univ. of TX System, Austin, Tex.

[21] Appl. No.: 08/960,365

[22] Filed: Oct. 29, 1997

Related U.S. Application Data

[62] Division of application No. 08/588,586, Jan. 18, 1996, Pat. No. 5,789,442.

[51] Int. Cl.$^7$ .................................................. A61K 31/195
[52] U.S. Cl. ......................... 514/561; 514/182; 514/177; 514/178; 514/179; 514/180; 514/181; 514/21; 514/412; 514/12; 514/645
[58] Field of Search ................................... 514/182, 177, 514/178, 179, 180, 181, 561, 21, 412, 12, 645

[56] References Cited

U.S. PATENT DOCUMENTS

| | | | |
|---|---|---|---|
| 5,260,276 | 11/1993 | Cody et al. | 514/14 |
| 5,378,715 | 1/1995 | Stein et al. | 514/329 |

FOREIGN PATENT DOCUMENTS

| | | |
|---|---|---|
| 93/10144 | 5/1993 | WIPO . |
| 93/25580 | 12/1993 | WIPO . |
| 95/00537 | 1/1995 | WIPO . |
| 95/02408 | 1/1995 | WIPO . |
| 95/06466 | 3/1995 | WIPO . |
| 95/13800 | 5/1995 | WIPO . |
| 95/13802 | 5/1995 | WIPO . |
| 95/22345 | 8/1995 | WIPO . |

OTHER PUBLICATIONS

Fabregues et al., Hypertension 19 (2 Suppl): 129–131 (Feb. 1992).
Schoenfeld et al., American Journal of Obstetrics and Gynecology 161(5): 1204–1205 (Nov. 1989).
Garfield et al., "Reversal of Preeclampsia Symptoms Induced in Rats by Nitric Oxide Inhibition With L–Arginine, Steroid Hormones and an Endothelin Antagonist," Soc. Gynecol. Invest. Abst. P384 (1994).
Chwalisz et al., "Estradiol Inhibits the Onapristone–Induced Preterm Parturition in Guinea Pigs by Blocking Cervical Ripening," J. Soc. Gynecol. Invest., vol. 2, No. 2, Mar. 1995.
Chwalisz et al., "Role of Progesterone During Pregnancy: Models of Parturition and Preeclampsia," Z. Geburtshilfe Perinatol, vol. 198, No. 5–5, pp. 170–180, 1994.
Richard et al., "In Vivo Evidence of an Endothelin–Induced Vasopressor Tone After Inhibition of Nitric Oxide Synthesis in Rats," Circulation, vol. 91, No. 3, pp. 771–775, Feb. 1995.
Yallampalli et al., Inhibition of Nitric Oxide Synthesis in Rats During Pregnancy Produces Signs Similar to Those of Preeclampsia, Am J Obstet. Gynecol, vol. 169, No. 5, pp. 1316–1320, 1993.
Yallampalli et al., "Uterine Contractile Responses to Endothlin–1 and Endothelin Receptors are Elevated During Labor," Biol Reprod, vol. 51, No. 4, pp. 640–645, 1994.
Bayhi et al., J. Clin. Anesth., 4:487–488 (1992).
Conrad, FASEB, 7:566–571 (1993).
Diamond, J. of Pharm. & Exp. Thera., 168(1):21–30 (1969).
Garfield et al., "Control of Myometrial Contractility and Labor," Basic Mechanisms Controlling Term and preterm Labor, Springer–Verlag Berlin,eds. Chwalisz et al.
Yallampalli et al., Soc. Gynecol. Invest. Abst. P41 (1993).
Greenspoon et al., Lancet, 338:124 (1991).
Izumi et al., Am. J. Obstet. Gynecol., 170:236–245 (1994).
Jennings et al., J. of Mat. Fetal Med., 2:170–175 (1993).
Lees et al., Lancet, 343:1325–1326.
Natuzzi et. al., Biochem. & Biophys. Res. Comm., 194(1):1–8 (1993).
Papka et al., Neuroscience Letters, 147:224–228 (1992).
Ramsay et al., Europ. J. of Clinical Investigation, 24:76–78 (1994).
Sladek et al., Am. J. Obstet. Gynecol., 169:1285–1291 (1993).
Yallampalli et al., Endocrinology, 133 (4):1899–1904 (1993).
Yallampalli et al., Endocrinology, 134 (4):1971 (1994).
Yallampalli et al., Am J. Obstet. Gynecol., 170:175–185 (1993).
Parlani et al., J. Pharm. & Exp. Thera., 265(2):713–719 (1993).
Andersson et al., Scand. J. Urol. & Nephro., 175:43–53 (1995).
Burnett et al., Urology, 45(6):1071–1078 (1995).
Ehren et al., Urology, 44(5):683–687 (1994).
Dokita et al., Life Sciences, 48(25):2429–2436.
Bennet et al., J. Urology, 153(6):2004–2009 (1995).
Versi et al., Curr. Probl Obst., 17(6):196–229 (1994).
Cardozo et al., Physiotherapy, 80(3):135–138 (1994).
Brandeis et al., Drup Therapy, 22:93–96 (1992).
Andersson et al., World J. Urology, 12(15) 274–280 (1994).

Primary Examiner—Jean C. Witz
Attorney, Agent, or Firm—Millen, White, Zelano & Branigan, P.C.

[57] ABSTRACT

The invention provides a method for the treatment and prevention of urinary incontinence in mammals, e.g., human males and females, especially nonpregnant female mammals, by administering a nitric oxide synthase substrate and/or nitric oxide donor, alone or in combination with an estrogenic agent and/or a progestational substance, with or without supplementation with an alpha-adrenergic agonist, beta-adrenergic receptor blocking agent, cholinergic-receptor blocking compound or a cholinergic-receptor-stimulating drug, as well as pharmaceutical compositions useful in practicing the methods of this invention.

9 Claims, 2 Drawing Sheets

TREATMENT OF URINARY INCONTINENCE WITH NITRIC OXIDE SYNTHASE SUBSTRATES AND/OR NITRIC OXIDE DONORS ALONE OR IN COMBINATION WITH ESTROGEN OR PROGESTERONE AND/OR OTHER AGENTS

This is a division of the application Ser. No. 08/588,586 filed Jan. 18, 1996 now U.S. Pat. No. 5,789,482.

BACKGROUND OF THE INVENTION

This invention relates to a method for the treatment and/or prevention of urinary incontinence usually in women during the post menopausal period or during pregnancy or postpartum with a nitric oxide synthase substrate (e.g., L-arginine), a nitric oxide donor or both, alone or in combination with estrogen and/or progestin (e.g., hormone replacement therapy (HRT)), or with supplementation with alpha-adrenergic agonists, beta-adrenergic receptor blocking agents, cholinergic-receptor-blocking compounds and/or cholinergic-receptor-stimulating drugs.

Women in industrialized nations can now expect to spend over a third of their lives in the postmenopausal period. One of the major problems women face during the climacteric period is urinary incontinence. Urinary incontinence is also a problem during pregnancy or postpartum. In pregnancy, this condition may be related to altered steroid and nitric oxide levels rather than the physical presence and pressure of the growing fetus.

Urinary incontinence is the inability of the bladder to retain urine resulting in urine loss as a consequence of either urge (urge incontinence), or physical or mental stress (stress incontinence). There have been many studies of the effects of estrogen and progesterone therapy for incontinence (Barbieri, 1994; Sartori et al., 1995). These studies indicate that estrogen and/or progesterone replacement therapy can partially alleviate incontinence in some women (Elia and Bergman, 1993; Sartori et al, 1995). However, there is no conclusive evidence that hormone therapy alone is sufficient to cure incontinence (Cardozo and Kelleher, 1995). Some studies have shown that hormone replacement therapy helps prevent postmenopausal recurrent urinary tract infections and improves urinary incontinence (Cardozo and Kelleher, 1994). Other studies suggest hormone supplementation with alpha-adrenergic agonists, beta-adrenergic-receptor blocking agents, cholinergic-receptor-blocking compounds and cholinergic-receptor-stimulating drugs (Barbieri, 9194; Brandeis and Resnick, 1992).

The normal bladder fills at a physiological rate dictated by the function of the kidneys and the bladder can accommodate large volumes of urine. This phenomenon has been attributed to physical properties of the bladder as well as a neural inhibitory system. The inhibitory mechanism may involve inhibition of parasympathetic activity or an increase in sympathetic tone to produce detrusor relaxation and allow filling to occur. During filling the outlet neck of the bladder and urethra are contracted preventing leakage. Voiding or micturition is characterized by a-relaxation of the outlet neck and the urethra followed by contraction of the detrusor muscle. The process begins again when the bladder is empty and the detrusor relaxes and the outlet neck and urethra contract to seal off the bladder and maintain continence.

It is now well known that HRT (hormone replacement therapy), such as estrogen treatment, improves or reverses the adverse effects of the decrease of sex steroid secretion by the ovaries during menopause. Estrogens have also been shown to improve mood and psychological well-being in postmenopausal women and they also prevent atrophic changes in the urogenital tract. Estrogens have been shown to effect arterial tone and this may help to explain the reduction in hot flushes observed in postmenopausal women with estrogen therapy. On the other hand, unopposed estrogen therapy has been associated with endometrial hyperplasia and endometrial cancer. Many studies have shown that the addition of progesterone to estrogen HRT decreases the risk of endometrial cancer and even reverses endometrial hyperplasia. However, progestins are not without their own untoward side effects. Progestins may reinforce the beneficial effects of estrogens on the cardiovascular system. Modern HRT now employs combinations of an estrogen and a progestin as in the general case for most contraceptives.

One of the most exciting recent advances in biology and medicine is the discovery that nitric oxide is produced by endothelial cells and that it is involved in the regulation of vascular tone, platelet aggregation, neurotransmission and immune activation (Furchgott and Zawadzki, 1980; Moncada, Palmer and Higgs, 1991; Ignarro, 1991). Nitric oxide is an important mediator of relaxation of the muscular smooth muscle (Montada, Palmer and Higgs, 1991) and was formerly known as EDRF (endothelin-derived relaxing factor) (Furchgott and Zawadzki, 1980; Moncada, Palmer and Higgs, 1991). Nitric oxide is synthesized by the oxidative deamination of a guanidino nitrogen of L-arginine by at least three different isoforms of a flavin-containing enzyme, nitric oxide synthase (Montada, Palmer and Higgs, 1991). Synthesis of nitric oxide has been shown to be competitively inhibited by analogues of L-arginine; NG-nitro-L-arginine methyl ester (L-NAME), NG-monoethyl-L-arginine (LMMA), N-iminoethyl-L-ornithine (L-NIO), L-monomethyl-L-arginine (L-NNMA) and L-NG-methylarginine (LNMA) and Nw-nitro-L-arginine (L-NA).

Nitric oxide elevates levels of cGMP (1,4,5-cyclic guanosine monophosphate) within the vascular smooth muscle to produce relaxation and to reduce blood vessels tone (Moncada, Palmer and Higgs, 1991). Nitric oxide binds to heme and thus activates soluble guanylate cyclase (Ignarro, 1991) to increase the cellular content of cGMP. It has long been recognized that nitrovasodilators, such as nitroprusside and nitroglycerin, inhibit vascular smooth muscle contractility to produce relaxation or to reduce vascular tone. These agents have been used since the late 1980s as vasodilators. However, only recently has the mechanism of action of these compounds been realized. Nitrovasodilators are now classified as nitric oxide donors because they are metabolized or spontaneously release nitric oxide (Moncada, Palmer and Higgs, 1991). The long-used nitrovasodilators may be regarded as substitution therapy for a failing physiological mechanism. Nitric oxide is also produced by macrophages and other immune cells.

There is a substantial body of evidence from animal experiments that a deficiency in nitric oxide contributes to the pathogenesis of a number of diseases, including hypertension, atherosclerosis and diabetes (Montada, Palmer and Higgs, 1991). There are many recent studies showing that the inhibition of nitric oxide synthase dramatically increases blood pressure.

Nitric oxide may also be involved in accommodation of the bladder during filling or relaxation of the bladder neck and urethra during voiding. The bladder is innervated by nonadrenergic and noncholinergic nerves (NANC nerves) and nitric oxide is thought to be a neurotransmitter in these types of nerves (Ehren et al, 1994; Andersson and Persson, 1994; Smet, et al, 1994; Lee et al., 1994). There is evidence showing that nitric oxide containing nerves are localized to a greater extent in the outlet region and urethra compared to the detrusor (Andersson and Persson, 1994; Lee et al., 1994). However, whether nitric oxide is involved in voiding by relaxing the urethra and bladder neck or in bladder filling by relaxing the detrusor is unclear. There have been few studies of the effects of nitric oxide donors on either the urethra, bladder neck or detrusor muscle.

SUMMARY OF THE INVENTION

Our studies suggest that nitric oxide donors effectively relax the detrusor muscle (see below). Further our studies of the uterus, cervix and vascular tissues suggest that the steroid hormones control nitric oxide synthesis, release and the effector system for nitric oxide (Chwalisz and Garfield, 1994). Therefore, we have discovered that the substrate for nitric oxide, nitric oxide donors, or both in combination with steroid hormones (estrogen and/or progesterone) are useful for treatment and prevention of urinary or urethra incontinence.

It is an object of the invention to provide a method for the treatment and prevention of urinary incontinence with a nitric oxide substrate and/or donor in mammals, e.g., human males and females, especially nonpregnant female mammals.

It is another object of the invention to provide a method for treatment and prevention of urinary incontinence with a nitric oxide substrate and/or donor in pregnant or postpartum female mammals.

It is a further object of the invention to provide a method for treatment and prevention of urinary incontinence with a nitric oxide substrate and/or donor in which an estrogenic agent in combination with a nitric oxide substrate and/or donor is used for urinary incontinence in both nonpregnant or pregnant female mammals.

It is a further object of the invention to provide a method for treatment and prevention of urinary incontinence with a nitric oxide substrate and/or donor in which a partial estrogenic agent (e.g. raloxifen) in combination with a nitric oxide substrate and/or donor is used for urinary incontinence in both nonpregnant or pregnant female mammals.

In another aspect of this invention, a progestational agent is used in combination with a nitric oxide substrate and/or nitric oxide donor for treatment and prevention of urinary incontinence in female mammals.

In a further aspect of this invention, an estrogen and a progestin are used in combination with a nitric oxide substrate and/or nitric oxide donor for the treatment and prevention of urinary incontinence in female mammals.

It is another object of this invention to provide a method for the treatment and prevention of urinary incontinence with a nitric oxide substrate and/or nitric oxide substrate alone or in combination with an estrogenic agent and/or a progestational substance, and with or without supplementation with an alpha-adrenergic agonist, beta-adrenergic receptor blocking agent, cholinergic-receptor blocking compound or a cholinergic-receptor-stimulating drug.

A further object is to provide pharmaceutical compositions useful in practicing the methods of this invention. Upon further study of the specification and appended claims, further aspects, objects and advantages of this invention will become apparent to those skilled in the art.

Thus, in a method aspect, this invention relates to a method of treating urinary incontinence in a mammal, e.g., nonpregnant or pregnant female mammal, which comprises administering to an individual manifesting the symptoms thereof one or both of a nitric oxide substrate and a nitric oxide donor, alone or in combination with an estrogen or a progestin, or both, and with or without supplementation with an alpha-adrenergic agonist, a beta-adrenergic receptor blocking agent, a cholinergic-receptor blocking compound or a cholinergic-receptor stimulating drug, all in amounts effective to ameliorate the symptoms thereof; typically, the amount of the nitric oxide synthase substrate and nitric oxide donor or both is effective to increase urinary continence by raising the blood level of circulating L-arginine in a female to whom the composition is administered to at least 10 to 500 $\mu$mole above the normally 50 to 1000 $\mu$mole circulating levels, or to raise nitric oxide donor levels to about 10 nM to 100 $\mu$M (micromolar), the amount of the estrogen being bioequivalent to approximately 2 mg per day of estradiol (e.g., Progynova, Schering), the amount of a partial estrogen being bioequivalent to approximately 1–200 mg per day of raloxifen, and the amount of the progestational agent administered being bioequivalent to 50–300 mg of injected progesterone.

In a product aspect, this invention relates to a pharmaceutical composition comprising at least one of a nitric oxide synthase substrate (L-arginine) and a nitric oxide donor (eg. sodium nitroprusside or glyceryl trinitrate), alone or in further combination with one or more of a estrogen and/or progestin with and without added supplements of an alpha-adrenergic agonist, a beta-adrenergic receptor blocking agent, a cholinergic receptor blocking compound or a cholinergic stimulating drugs with the amount of the nitric oxide synthase substrate, a nitric oxide donor or both per unit dosage being equivalent to either raise the blood level of circulating L-arginine to least 10 to 500 $\mu$mole above the normally 50 to 1000 $\mu$mole circulating or raise nitric oxide donor levels to about 10 nM to 100 $\mu$M, the amount of the estrogen being bioequivalent to about 2 mg of estradiol (e.g., Progynova, Schering), the amount of a partial estrogen being bioequivalent to approximately 1–200 mg per day of raloxifen, with the amount of the progesterone bioequivalent to 50 to 300 mg of injected progesterone and the amount of the supplemental alpha-adrenergic agonist, beta-receptor blocking agent, cholinergic-receptor blocking compound or cholinergic stimulating drug as indicated below.

The methods of this invention treat urinary incontinence in a menopausal/postmenopausal, nonpregnant or pregnant, and/or postpartum female, who is manifesting the symptoms thereof.

Because the conditions of menopause/postmenopause, pregnancy or postpartum are produced or aggravated by subnormal nitric oxide synthesis, both nitric oxide synthase substrates, e.g., L-arginine and nitric oxide donors, e.g., sodium nitroprusside, nitroglycerin, glyceryl trinitrate, SIN-1, isosorbid mononitrate, isosorbid dinitrate and diethylenetriamine/NO (DETA/NO), are useful for ameliorating the symptoms thereof and, in one respect of this method of this invention, a combination of both are employed.

An additive effect is achieved when an estrogenic agent is administered concurrently with a nitric oxide substrate and/or nitric oxide donor. In the case of a female mammal, an estrogen can be administered concurrently with or in lieu of a progestin. The latter can also be used alone.

An additional effect is achieved when a nitric oxide substrate or a nitric oxide donor is administered either with estrogen or progestin and supplemented with one of a alpha-adrenergic agonist, a beta receptor blocking agent, a cholinergic-receptor blocking agent or a cholinergic stimulating drug.

Thus, the method aspects of this invention and the pharmaceutical composition aspects of this invention employ either or both of a nitric oxide substrate and a nitric oxide donor and, optionally one or more of, e.g., an estrogen (e.g., Progynova, Schering) or a progestin (e.g., progesterone or norgestrel), with or without one of the following: an alpha-adrenergic agonist, a beta-receptor blocking agent, a cholinergic-receptor blocking compound-or a cholinergic stimulating drug.

Examples of dosage ranges of typical NO-substrates and NO-donors (per os or transdermally) are:

|  | total dose: |
|---|---|
| L-Arginine | 500 mg–10 g p.o. |
| Sodium Nitroprusside | range 500–2000 μg/kg/day p.o. |
| Nitroglycerin | 0.5–10 mg p.o. |
| Nitroglycerin | 0.1–10 mg/24 hours transdermal |
| Isosorbid mononitrate | 10–100 mg/day p.o. |
| Isosorbid dinitrate | 100 mg/mg p.o. |

The nitric oxide donors (e.g., nitroglycerin) can be administered preferentially by a transdermal patch (e.g., Deponit 5/10/T [Schwarz Pharma], Nitroderm TTS 5/Nitroderm TTS 10 [CIBA]), orally (e.g., Corangin [CIBA], Nitrolingual forte or mitte [Pohl],) etc.

Examples of combinations of active agents which can be administered concurrently with a nitric oxide substrate and/ or nitric oxide donor are the following estrogens and progestins and typical oral dosage ranges of the active agents of the estrogen and progestin type with the nitric oxide substrate or donor:

Estrogens: A daily dose bioequivalent to about 1–2 mg per day estradiol, e.g., Premarin, Wyeth-Ayerst, 0.625 mg/day; estradiol valerate, 50, μg/day transdermally; vaginal estradiol creams, 1.25 mg/day and vaginal estradiol rings, 0.2 mg/day and the natural occurring estrogens used in hormone replacement therapy currently available.

Partial estrogen agonists (partial estrogens): A daily dose bioequivalent to about 1–200 mg per day, e.g. raloxifen ([6-hydroxy-2-(4-hydroxyphenyl)-3-benzothienyl][4-[2-(1-piperidinyl)ethoxy]phenyl]methanon-hydrochloride), tamoxifen ((Z)-N,N-dimethyl-2-[4-( 1,2-diphen-yl-1-butenyl)phenoxy]ethanamine, nafoxidin (1-[2-[4-(3,4-dihydro-6-methoxy-2-phenyl-1-naphthalinyl)phenoxy] ethyl]pyrrolidin-hydrochloride), Mer-25 (a-[4-[2-(diethylamino)ethoxy]phenyl]-4-methoxy-a-phenyl-benzenethanol) and centchroman ((3R-trans)-3,4-dihydro-2, 2-dimethyl-7-methoxy-3-phenyl-4-[4-[2-( 1-pyrrolidinyl) ethoxy]phenyl]-2H-1-benzopyran).

Progestins: A daily dose bioequivalent to 50–300 mg of progesterone/day, e.g., an injectable suspension of medroxyprogesterone acetate to provide a weekly dose thereof of 100–1000 mg or tablets or dragees providing an oral dose thereof of 5–100 mg/day, an injectable solution of hydroxyprogesterone caproate which provides a weekly dose of 250–500 mg; tablets, capsules or dragees of norethindrone acetate which provide a daily dose of 5–20 mg.

Examples of estrogen and progestin combinations are listed below:

| Product | Composition | Dose (mg per day) |
|---|---|---|
| Climaval (Sandoz) | Estradiol valerate | 1 or 2 |
| Progynova (Schering) | Estradiol valerate | 1 or 2 |
| Harmogen (Abbott) | Piperazine estrone | 1.05 or 2.5 |
| Hormonin (Shire) | Estradiol + Estrone + Estriol | 0.6 |
| Premarin (Wyeth-Ayerst) | Conjugated equine Estrogens | 0.625, 1.25 or 2.5 |

Commercially available combination calendar packs for hormone replacement therapy include "Estrapak", "Prempak-C!", "Trisequens", "Trisenquens forte" and "Cycloprogynova". The following are illustrative compositions of such products:

Estradiol 50 mg per day (28 days, 8 patches) conjugated equine estrogens 0.625 mg per day (28 days)

Estradiol valerate 2 mg per day (11 days)

Estradiol valerate 2 mg per day

Norgestrel 0.5 mg per day (10 days)

Norgestrel 0.1 5 mg per day (12 days) conjugated equine Estrogens 1.25 mg per day (28 days)

Norgestrel 0.15 mg per day (12 days) estradiol 2 mg per day+estriol 1 mg per day (22 days)

Norethisterone acetate 1 mg per day (10 days) estradiol 1 mg per day+estriol 0.5 mg per day (6 days) estradiol 4 mg per day+estriol 2 mg per day (21 days)

Norethisterone acetate 1 mg per day (10 days)

Estradiol 1 mg per day+estriol 0.5 mg per day (6 days)

Estradiol valerate 1 mg per day (21 days)

Levonorgestrel 0.25 mg per day (10 days)

Estradiol valerate 2 mg per day (21 days)

Levonorgestrel 0.5 mg per day (10 days)

Daily doses of progestogens taken for 12 days per month in patients receiving oral or transdermal estrogens:

| Norethisterone | 0.7–2.5 mg per day |
|---|---|
| Medroxyprogesterone acetate | 10 mg per day |
| Norgestrel | 150 μg per day |
| Dydrogesterone | 10–20 mg per day |

Typical dosages of exemplary supplemental agents include those shown below, other bioequivalent amounts of analogous such agents being routinely determinable:

Alpha-adrenergic-receptor-agonists:
Phenylpropanolamine 25–100 mg daily
Phenylephrine 5–15 mg daily
Beta-receptor-blocking agents:
Propranolol 20–120 mg daily
Befaxolol 10–40 mg daily
Acebutolol 400 mg daily
Atenolol 50–100 mg daily
Bisoprolol 5–10 mg daily
Cholinergic-receptor blocking compounds:
Benztropine 0.5–1 mg daily
Biperiden 3–6 mg daily
Propantheline 30–120 mg daily
Cholinergic-stimulating drugs:
Bethanecol 30–120 mg daily Many other examples of compounds in each of the four foregoing categories are well known and can be employed in this invention.

The pharmacologically active agents employed in this invention can be administered in admixture with conventional excipients, i.e., pharmaceutically acceptable liquid, semi-liquid or solid organic or inorganic carriers suitable, e.g., for parental or enteral application and which do not deleteriously react with the active compound in admixture therewith. Suitable pharmaceutically acceptable carriers include but are not limited to water, salt solutions, alcohols, vegetable oils, polyethylene glycols, gelatin, lactose, amylose, magnesium stearate, talc, silicic acid, viscous paraffin, perfume oil, fatty acid monoglycerides and diglycerides, pentaerythritol fatty acid esters, hydroxy methylcellulose, polyvinyl pyrrolidone, etc.

The pharmaceutical preparations can be sterilized and if desired mixed with auxiliary agents, e.g., lubricants, preservatives, stabilizers, wetting agents, emulsifiers, salts for influencing osmotic pressure, buffers, coloring, flavoring and/or aromatic substances and the like which do not deleteriously react with the active compounds.

For parental application, particularly suitable are solutions, preferably oily or aqueous solutions, as well as suspensions, emulsions, or implants, including suppositories, transdermal patches, and vaginal gels, creams and foams. Ampoules are convenient unit dosages.

In a preferred aspect, the composition of this invention is adapted for ingestion.

For enteral application, particularly suitable are unit dosage forms, e.g., tablets, dragees or capsules having talc and/or carbohydrate carrier or binder or the like, the carrier preferably being lactose and/or corn starch and/or potato starch; particulate solids, e.g., granules; and liquids and semi-liquids, e.g., syrups and elixirs or the like, wherein a sweetened vehicle is employed. Sustained release compositions can be formulated including those wherein the active compound is protected with differentially degradable coatings, e.g., by microencapsulation, multiple coatings, etc.

Suitable for oral administration are, inter alia, tablets, dragees, capsules, pills, granules, suspensions and solutions. Each unit dose, e.g., each tablespoon of liquid or each tablet, or dragee contains, for example, 5–5000 mg of each active agent.

Solutions for parenteral administration contain, e.g., 0.01–1% of each active agent in an aqueous or alcoholic solution.

The nitric oxide substrate and/or donor can be administered as an admixture with an estrogen and/or progestational agent and/or any other optional active agent or as a separate unit dosage-form, either simultaneously therewith or at different times during the day from each other.

The combination of active agents is preferably administered at least once daily (unless administered in a dosage form which delivers the active agents continuously) and more preferably several times daily, e.g., in 2 to 6 divided doses. The typical dose is about 0.5 to 1000 mg of each active agent, although some less active agents, e.g., L-Arginine, require much higher oral dosages, e.g., 500 to 10,000 mg, and others, e.g., sodium nitroprusside, require lower doses, e.g., 500–2,000 µg/kg/day. Doses for nitroglycerine typically are orally 2.6 mg 2×daily; sublingually, 0.8 mg 1–4×daily; and transdermally, 0.2–0.5 mg/hr. Since the $LD_{50}$ dosages of most of these active agents is known in the prior art, a lower dosage regimen can be initiated and the dosage increased until a positive effect is achieved or a higher dosage regimen can initially be employed, e.g., in a crisis situation, and the dosages regulated downward as relief from the symptoms is achieved. Combinations of agents can be employed either continuously or sequentially.

In humans, both L-arginine and progesterone (or bioequivalent of another progestin) should be given in a ratio which produces blood plasma levels of 50–5000 µmolar L-arginine, 30–100 nmolar progesterone and 500 to 1000 nmolar of estradiol.

BRIEF DESCRIPTION OF THE DRAWINGS

Various other objects, features and attendant advantages of the present invention will be more fully appreciated as the same becomes better understood when considered in conjunction with the accompanying drawings, in which like reference characters designate the same or similar parts throughout the several views, and wherein:

FIG. 1 shows the effects of sodium nitroprusside (SNP) ($10^{-3}$M) on contractions of the rat detrusor muscle after stimulating the muscle with methylcholine (MC at $10^{-6}$M and $10^{-5}$M).

DETAILED DESCRIPTION OF THE INVENTION

Figure 1:
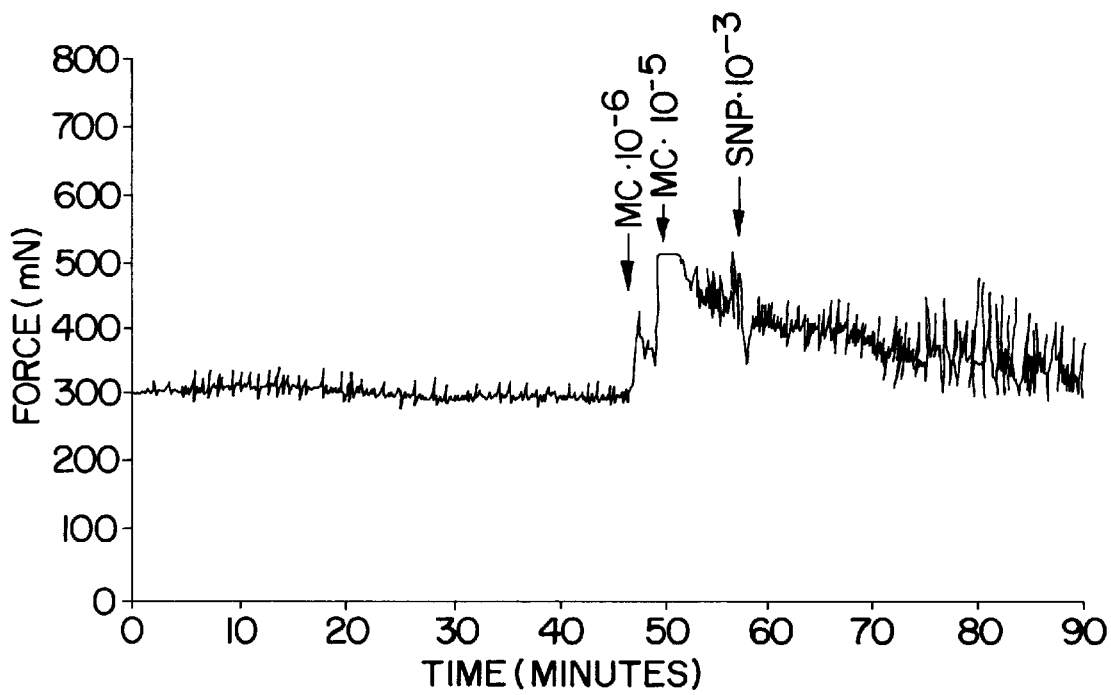
FIG. 1.
Figure 2:
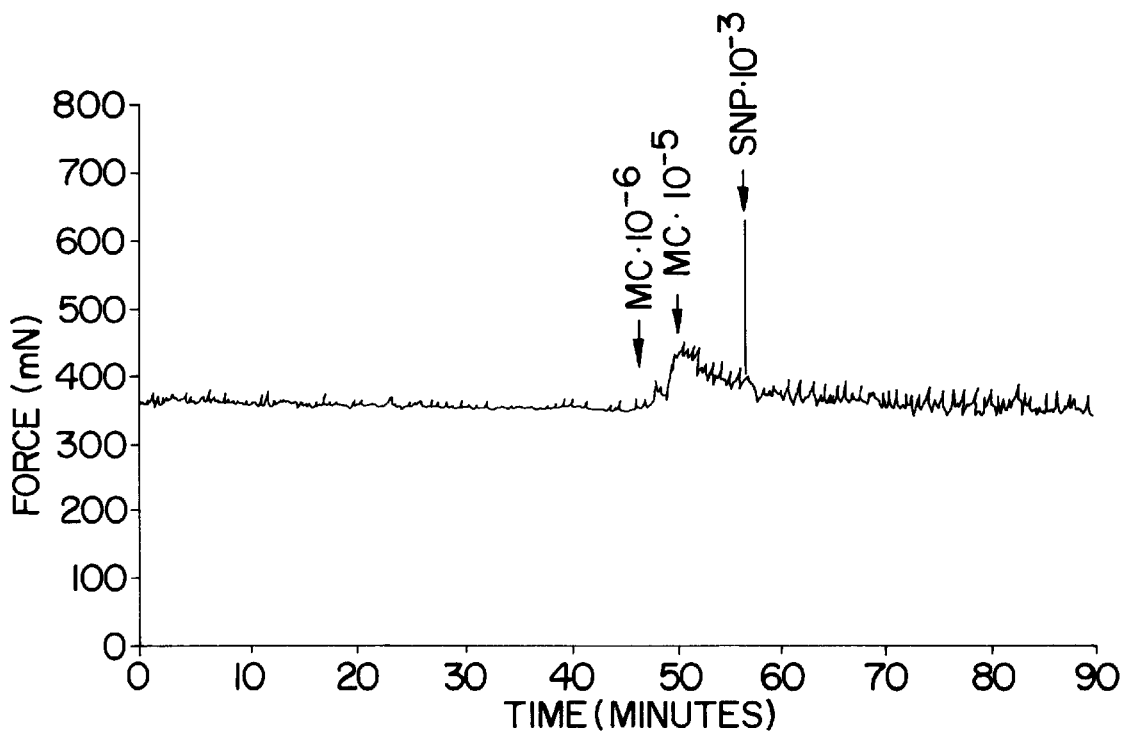
FIG. 2: Data similar to FIG. 1 is demonstrated in FIG. 2.

In the experiments whose results are shown in FIG. 1, rat bladder detrusor muscle was obtained from ovariectomized and normal non-pregnant animals. The tissues were suspended in muscle baths to record in vitro contractility and drugs were added to the baths to estimate their effects on the mechanical events. In the experiments shown in FIGS. 1 and 2, methylcholine (MC at $10^{-6}$M and $10^{-5}$M) was added to precontract the bladder samples, then the nitric oxide donor sodium nitroprusside (SNP at $10^{-3}$M) was added to the bath. SNP caused an immediate and significant decrease in contractility. The relaxation response was transient which is typical of SNP for this preparation. Similar data was obtained from 16 other strips of tissues suspended in vitro and treated with SNP.

Figure 3:
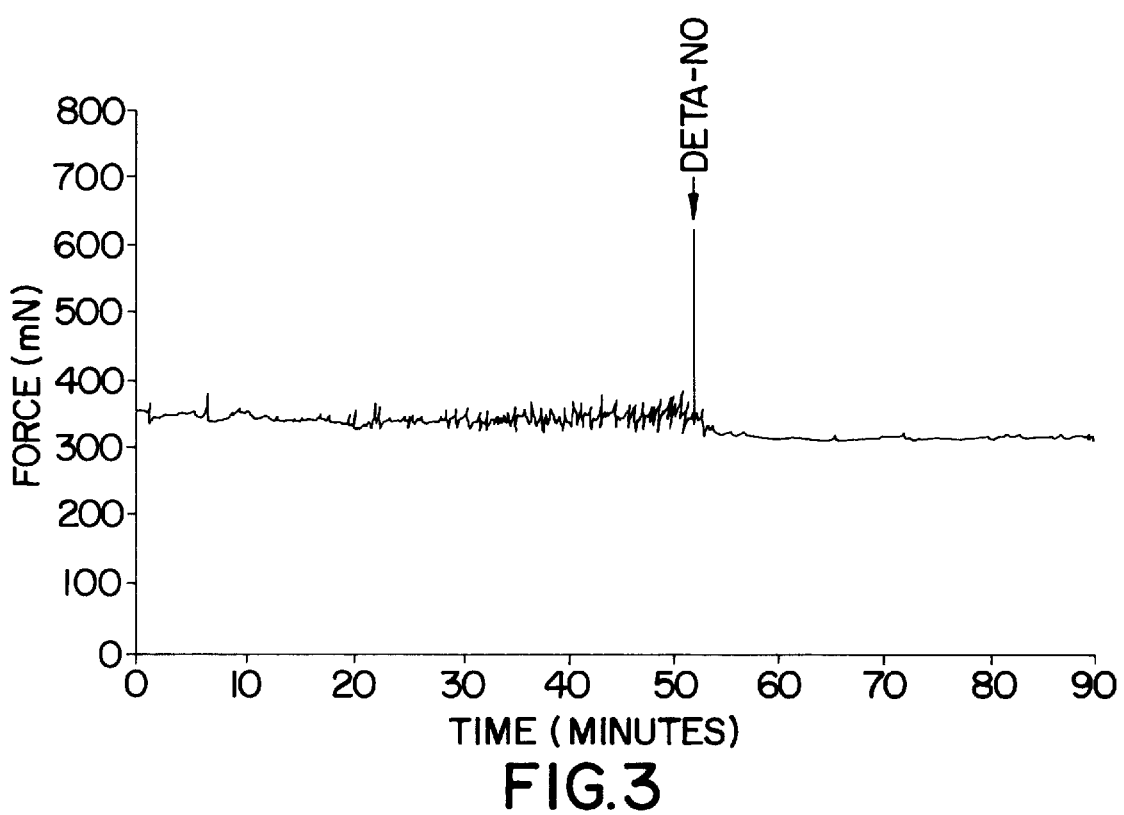
FIG. 3: Effects of DETA/NO (diethylenetriamine/NO) a nitric oxide donor compound on spontaneous contractions of the rat detrusor muscle.

In the results shown in FIG. 3,, tissues were contracting spontaneously in vitro. When DETA/NO, a nitric oxide donor compound, was added to the muscle bath, spontaneous contractions abruptly disappeared and did not reappear during the recording period, about 30 minutes. Similar results were obtained from tissues from 16 rats. Additionally, tissues from ovariectomized rats treated with estrogen showed more pronounced effects than untreated ovariectomized rats (n=8).

It can be concluded from these results that nitric oxide has a profound relaxation effect on the rat detrusor muscle. Since L-arginine is the substrate for nitric oxide one can deduce that nitric oxide substrates will also relax detrusor muscle. Further, since the effects of nitric oxide are much greater after treating rats with estrogen it can be concluded that estrogen plus a nitric oxide donor or a nitric oxide substrate may have greater effects when an nitric oxide substrate or donor are combined with estrogen. Furthermore, since estrogen and progesterone often act synergistically one can infer that estrogen and/or progesterone combinations would be useful. Relaxation of the detrusor muscle with nitric oxide donors indicates that nitric oxide may be involved in detrusor relaxation during the filling phase of bladder function. Therefore, nitric oxide donors and/or substrates alone or in combination with steroids will prove effective for urinary incontinence. Furthermore, since the bladder is innervated by adrenergic and cholinergic nerves combinations with alpha adrenergic agonists, beta-receptor blocking agents, cholinergic-blocking compounds or cholinergic stimulating drugs will be useful to treat incontinence.

Without further elaboration, it is believed that one skilled in the art can, using the preceding description, utilize the present invention to its fullest extent. The following preferred specific embodiments are, therefore, to be construed as merely illustrative and not limitative of the remainder of the disclosure in any way whatsoever.

In the foregoing and in the following examples, all temperatures are set forth uncorrected in degrees Celsius; and, unless otherwise indicated, all parts and percentages are by weight.

The entire disclosures of all applications, patents and publications, cited above and below, if any, are hereby incorporated by reference.

EXAMPLES

Example 1
Treatment of Urinary Incontinence

To a nonpregnant human female (ca 60 years; 50–90 kg) displaying the signs of menopause or postmenopausal symptoms, including amenorrhea, and urinary incontinence, administer L-arginine 0.5 to 20 g of L-arginine per os daily in three divided doses until the symptoms are ameliorated. Thereafter, administer 0.5 to 5 g of L-arginine daily.

Example 2
Treatment of Urinary Incontinence

To a female comparable to and displaying the same symptoms as Example 1, administer daily 5–10 mg of nitroglycerine transdermally.

Example 3
Treatment of Urinary Incontinence

To a female comparable to and displaying the same symptoms as Example 1, administer daily 2×2.5 mg of nitroglycerine orally.

Example 4
Treatment of Urinary Incontinence

To a female similar to and displaying the same symptoms as Example 1, administer daily 0.5 to 20 g of L-arginine in combination with estrogen (e.g., estradiol valerate) 1–2 mg daily.

Example 5
Treatment of Urinary Incontinence

To a female similar to and displaying the same symptoms as Example 1, administer daily 2×5 mg nitroglycerine transdermally in combination with a partial estrogen agonist (e.g., raloxifen) 100 mg daily.

Example 6
Treatment of Urinary Incontinence

To a female similar to and displaying the same symptoms as Example 1, administer daily 0.5 to 20 g of L-arginine in combination with a partial estrogen agonist (e.g., raloxifen) 100 mg daily.

Example 7
Treatment of Urinary Incontinence

To a female similar to and displaying the same symptoms as Example 1, administer daily 2×2.5 mg nitroglycerin with a progestin (e.g., norgestrel) 150 µg per day.

Example 8
Treatment of Urinary Incontinence

To a female comparable to and displaying the same symptoms as Example 1, administer L-arginine 0.5 to 20 g daily and/or a nitric oxide donor (e.g., nitroglycerine, 2×2.5 mg) daily with or without one of the following, an estrogen (e.g., estradiol valerate) 1–2 mg daily, on a progestin (e.g., norgestrel, at 150 mg per day). The latter sex steroids to be given either continuously with L-arginine and/or a nitric oxide-donor, or sequentially—the progestins taken for only 6–12 days per month.

Example 9
Treatment of Urinary Incontinence

To a female comparable to and displaying the same symptoms of Example 1, administer L-arginine (0.5 to 20 g daily) and/or a nitric oxide donor (e.g. nitroglycerine, 2×2.5 mg daily) with or without one or more of the following, an estrogen (e.g., estradiol valerate, 1–2 mg daily) or a progesterone (e.g. norgestrel, at 150 mg per day), an alpha-adrenergic agonist) (e.g. phenylpropanolamine, 25 to 100 mg daily), a beta-receptor blocking agent (e.g. propranolol 20–120 mg daily), a cholinergic receptor blocking compound (e.g. propantheline 30–120 mg daily) or a cholinergic stimulating drug (e.g. bethanecol 30–120 mg daily).

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

REFERENCES

1. Barbieri, R. L. The bladder in menopause: Lower urinary tract dysfunction during the climacteric. Curr. Problems Obstet. Gynecol. Fertil. 1994; 17(6}:196–228.
2. Eli, G. and Bergman, A. Estrogen effects on the urethra: beneficial effects in women with genuine stress incontinence. Obstet. Gynecol. 1993; 48(7):509–517.
3. Sartori, M. G., Baracat, E. C., Girad, M. J., Gonccalves, W. J., Sartori, J. P., de Lima, G. R. Menopausal genuine stress urinary incontinence treated with conjugated estrogens plus progestogens. Int. J. Gynecol. Obstet. 1995; 49(2):165–169.
4. Cardozo, L. D. and Kelleher, C. J. Sex hormones, the menopause and urinary problems. Gynecol. Endocrinol. 1995; 9(1):75–84.
5. Cardozo, L. and Kelleher, C. Sex hormones and the female lower urinary tract. Physiotherapy 1994; 80:135–138.
6. Brandeis, G. H. and Resnick, N. M. Pharmacotherapy of urinary incontinence in the elderly. Drug Therapy 1992; 22:93–102.
7. Furchgott, R. F. and Zawadzki, J. V. The obligatory role of endothelial cells in the relaxation of arterial smooth muscle by acetylcholine. Nature 1980; 288:373–376.
8. Moncada, S., Palmer, R. M. G. and Higgs, E. A. Nitric oxide; physiology, pathophysiology and pharmacology. Pharmacol. Rev. 1991; 43:109–142.
9. Ignarro, L. J. Physiological significance of Nitric oxide. Seminars in Perinatology 1991; 15:20–26.
10. Ehren, I., Adolfsson, J. and Wilund, N. P. Nitric oxide synthase activity in the human urogenital tract. Urol. Res. 1994; 22:287–290.

11. Andersson, K. E. and Persson, K. Nitric oxide synthase and nitric oxide mediated effects in lower urinary tract smooth muscles. World J. Urol. 1994; 12:274–280.
12. Smet, P. J., Edyvane, K. A., Jonavicius, J., Marshall, V. R. Distribution of NADPH-diaphorase-positive nerves supplying the human urinary bladder. J. Autonomic Nervous System 1994; 47:109–113.
13. Lee, J. G., Wein, A. J., Levin, R. M. Comparative pharmacology of the male and female rabbit bladder neck and urethra: Involvement of nitric oxide. Pharmacology
14. Chwalisz, K. and Garfield, R. E. Role of progesterone during pregnancy: Models of parturition and preeclampsia. Z. Geburtsh. u. Perinat. 198:170–180.

What is claimed is:

1. A pharmaceutical composition comprising an admixture of effective amounts of
   (a) a nitric oxide synthase substrate, a nitric oxide donor or both, and
   (c) one or more of an alpha-adrenergic agonist, a cholinergic blocking agent, and, optionally,
   (b) one or more of a beta-receptor blocking agent, a cholinergic stimulating drug, an estrogen or a progestin.

2. The composition of claim 1, wherein (a) comprises a nitric oxide synthesis substrate.

3. The composition of claim 2, wherein the nitric oxide syntheses substrate is L-arginine.

4. The composition of claim 1, wherein (a) comprises a nitric oxide donor.

5. The composition of claim 4, wherein the nitric oxide donor is sodium nitroprusside, nitroglycerin, glyceryl trinitrate, SIN-1, isosorbid mononitrate or isosorbid dinitrate.

6. The composition of claim 1, wherein (b) comprises an estrogen, which is estradiol valerate.

7. The composition of claim 1, wherein (b) comprises a progestin which is levonorgestrel.

8. The composition of claim 1, wherein the amounts of (a), (c) and optionally (b) are effective to ameliorate the symptoms of urinary incontinence in a menopausal or post-menopausal female mammal.

9. The composition of claim 1, wherein the effective amount of (a) comprises an amount of the nitric oxide synthase substrate, nitric oxide donor or both effective to raise the blood level of circulating L-arginine to at least about 50–5000 $\mu$molar above the normally 50–1000 $\mu$molar circulating levels or raise the nitric oxide donor levels to about 10 nM to 100 $\mu$molar, and the effective amount of (b) comprises an amount of estrogen equivalent to 1–2 mg of estradiol, an amount of progestin bioequivalent to 50–300 mg of injected progesterone, or both.

* * * * *